(12) United States Patent
Tewes et al.

(10) Patent No.: US 10,753,734 B2
(45) Date of Patent: Aug. 25, 2020

(54) DEVICE, METHOD AND SYSTEM FOR GENERATING DYNAMIC PROJECTION PATTERNS IN A CONFOCAL CAMERA

(71) Applicant: DENTSPLY SIRONA Inc., York, PA (US)

(72) Inventors: Michael Tewes, Bruhl (DE); Markus Berner, Bulach (CH)

(73) Assignee: DENTSPLY SIRONA Inc., York, PA (US)

( * ) Notice: Subject to any disclaimer, the term of this patent is extended or adjusted under 35 U.S.C. 154(b) by 35 days.

(21) Appl. No.: 16/003,628

(22) Filed: Jun. 8, 2018

(65) Prior Publication Data

US 2019/0376784 A1   Dec. 12, 2019

(51) Int. Cl.
*G01B 11/25* (2006.01)

(52) U.S. Cl.
CPC ...... *G01B 11/2513* (2013.01); *G01B 11/2518* (2013.01)

(58) Field of Classification Search
CPC ............ G01B 11/2518; G01B 11/2527; G01B 11/2536; G01B 11/005; G01B 11/25; G01B 11/2513; G01S 7/486; G01S 7/499; G01S 17/48; G01S 17/89; G01S 7/4815; G01S 7/4818; G01S 7/484; G01C 3/08; A61C 19/04; A61C 9/0053; A61B 1/24; A61B 1/00193; A61B 1/0646; A61B 1/00009
See application file for complete search history.

(56) References Cited

U.S. PATENT DOCUMENTS

| | | | |
|---|---|---|---|
| 4,626,893 A | 12/1986 | Yamanaka | |
| 5,339,154 A | 8/1994 | Joschim | |
| 5,856,667 A | 1/1999 | Spirig | |
| 5,963,667 A * | 10/1999 | Hashimoto | G06K 9/74 382/190 |
| 6,499,998 B2 | 12/2002 | Kerschbaumer | |
| 7,092,017 B2 | 8/2006 | Kelly | |
| 7,092,107 B2 | 8/2006 | Babayoff | |
| 7,259,874 B2 | 8/2007 | Cutler | |
| 7,312,924 B2 | 12/2007 | Trissel | |
| 7,319,529 B2 | 1/2008 | Babayoff | |
| 7,329,860 B2 | 2/2008 | Feng | |
| 7,511,829 B2 | 3/2009 | Babayoff | |

(Continued)

FOREIGN PATENT DOCUMENTS

CN    2473645 U    1/2002
CN    102945637 A    2/2013

(Continued)

OTHER PUBLICATIONS

Stephen Beer, Smart-Pixel Imager HELIOCT3, Preliminary Data Sheet V1.3, Aug. 3, 2009, 1-33, CSEM, Zurich.

*Primary Examiner* — Neil R Mikeska

(74) *Attorney, Agent, or Firm* — Dentsply Sirona Inc.

(57) ABSTRACT

A device, method and system for utilizing an optical array generator, confocal measurement/depth of focus techniques to generate dynamic patterns in a camera for projection onto the surface of an object for three-dimensional (3D) measurement. Projected light patterns are used to generate optical features on the surface of an object to be measured and optical 3D measuring methods which operate according to triangulation, confocal and depth of focus principles are used to measure the object.

14 Claims, 7 Drawing Sheets

(56) References Cited

U.S. PATENT DOCUMENTS

| | | | |
|---|---|---|---|
| 7,522,322 B2 | 4/2009 | Blanding | |
| 7,724,378 B2 | 5/2010 | Babayoff | |
| 7,852,492 B2 | 12/2010 | Markus | |
| 7,960,685 B2 | 6/2011 | Feng | |
| 8,102,538 B2 | 1/2012 | Babayoff | |
| 8,340,456 B1* | 12/2012 | DaneshPanah | H04N 5/23219 |
| | | | 382/255 |
| 8,363,228 B2 | 1/2013 | Babayoff | |
| 8,446,595 B2 | 5/2013 | Ertl | |
| 8,451,456 B2 | 5/2013 | Babayoff | |
| 8,558,873 B2* | 10/2013 | McEldowney | G01B 11/2513 |
| | | | 348/46 |
| 8,570,530 B2 | 10/2013 | Liang | |
| 8,638,447 B2 | 1/2014 | Babayoff | |
| 8,638,448 B2 | 1/2014 | Babayoff | |
| 8,665,257 B2 | 3/2014 | Moshe | |
| 8,675,207 B2 | 3/2014 | Babayoff | |
| 8,723,895 B2 | 5/2014 | Chen | |
| 8,848,991 B2 | 9/2014 | Tjioe | |
| 8,878,905 B2 | 11/2014 | Fisker | |
| 8,885,175 B2 | 11/2014 | Babayoff | |
| 8,971,999 B2 | 3/2015 | Kim | |
| 9,019,576 B2 | 4/2015 | Rosberg | |
| 9,066,772 B2 | 6/2015 | Tchouprakov | |
| 9,101,433 B2 | 8/2015 | Babayoff | |
| 9,192,305 B2 | 11/2015 | Levin | |
| 9,261,356 B2 | 2/2016 | Lampert | |
| 9,295,532 B2 | 3/2016 | Milch | |
| 9,347,772 B2 | 5/2016 | Park | |
| 9,349,182 B2 | 5/2016 | Milch | |
| 9,393,087 B2 | 7/2016 | Moalem | |
| 9,404,740 B2 | 8/2016 | Babayoff | |
| 9,427,162 B2 | 8/2016 | Friedman | |
| 9,431,887 B2 | 8/2016 | Boltanski | |
| 9,439,568 B2 | 9/2016 | Yossef | |
| 9,491,863 B2 | 11/2016 | Rami | |
| 9,522,054 B2 | 12/2016 | Kim | |
| 9,615,901 B2 | 4/2017 | Babayoff | |
| 9,625,258 B2 | 4/2017 | Deichmann | |
| 9,628,779 B2 | 4/2017 | Knut | |
| 9,660,418 B2 | 5/2017 | Yossef | |
| 9,675,429 B2 | 6/2017 | Lampert | |
| 9,675,430 B2 | 6/2017 | Verker | |
| 9,693,839 B2 | 7/2017 | Yossef | |
| 9,709,803 B2 | 7/2017 | Boltanski | |
| 9,717,402 B2 | 8/2017 | Lampert | |
| 9,769,455 B2 | 9/2017 | Fisker | |
| 9,801,698 B2 | 10/2017 | Levin | |
| 9,844,427 B2 | 12/2017 | Atiya | |
| 9,910,255 B2 | 3/2018 | Markus | |
| 9,931,188 B2 | 4/2018 | Gottfried | |
| 9,939,258 B2 | 4/2018 | Lampert | |
| 9,956,061 B2 | 5/2018 | Moalem | |
| 9,962,244 B2 | 5/2018 | Esbech | |
| 10,010,387 B2 | 7/2018 | Esbech | |
| 2003/0019931 A1* | 1/2003 | Tsikos | G02B 26/10 |
| | | | 235/454 |
| 2006/0072123 A1* | 4/2006 | Wilson | G01B 11/2518 |
| | | | 356/609 |
| 2010/0008588 A1* | 1/2010 | Feldkhun | G01B 11/2518 |
| | | | 382/206 |
| 2010/0085636 A1 | 4/2010 | Berner | |
| 2011/0058159 A1* | 3/2011 | Weston | G01B 11/24 |
| | | | 356/237.1 |
| 2011/0242281 A1* | 10/2011 | Schmidt | A61C 19/04 |
| | | | 348/46 |
| 2014/0218731 A1 | 8/2014 | Schick | |
| 2015/0009357 A1* | 1/2015 | Seibel | G02B 23/2469 |
| | | | 348/222.1 |
| 2015/0172513 A1 | 6/2015 | Noorkami | |
| 2015/0281671 A1* | 10/2015 | Bloom | G01B 11/2527 |
| | | | 348/46 |
| 2016/0000332 A1 | 1/2016 | Yossef | |
| 2016/0022389 A1 | 1/2016 | Esbech | |
| 2016/0295191 A1 | 10/2016 | Babayoff | |
| 2016/0327779 A1* | 11/2016 | Hillman | G02B 21/367 |
| 2016/0330365 A1 | 11/2016 | Maruyama | |
| 2017/0222404 A1 | 8/2017 | Yossef | |
| 2017/0231731 A1 | 8/2017 | Korten | |
| 2017/0252132 A1 | 9/2017 | Yossef | |
| 2017/0265970 A1 | 9/2017 | Verker et al. | |
| 2017/0311791 A1 | 11/2017 | Lampert | |
| 2017/0374350 A1 | 12/2017 | Fisker | |
| 2018/0025529 A1 | 1/2018 | Wu | |
| 2018/0027159 A1 | 1/2018 | Dillon | |
| 2018/0153664 A1 | 6/2018 | Esbech | |
| 2018/0192877 A1 | 7/2018 | Yossef | |

FOREIGN PATENT DOCUMENTS

| | | |
|---|---|---|
| CN | 103969326 B | 5/2016 |
| CN | 105791792 A | 7/2016 |
| CN | 105187810 B | 6/2017 |
| CN | 107277481 A | 10/2017 |
| CN | 104468578 B | 12/2017 |
| DE | 102016000415 A1 | 7/2017 |
| EP | 0837659 B1 | 11/1999 |
| EP | 1155663 B1 | 10/2004 |
| EP | 1327851 B1 | 11/2005 |
| EP | 2051042 B1 | 10/2007 |
| EP | 1941843 A3 | 7/2008 |
| EP | 1607064 B1 | 9/2008 |
| EP | 2439489 A2 | 11/2012 |
| EP | 2719160 A2 | 4/2014 |
| EP | 2729048 A1 | 5/2014 |
| EP | 2326915 B1 | 4/2015 |
| EP | 2956084 A1 | 12/2015 |
| EP | 2739206 B1 | 5/2017 |
| EP | 3068336 B1 | 8/2017 |
| EP | 3211403 A1 | 8/2017 |
| JP | 2016131378 A | 7/2016 |
| WO | 200780834 A1 | 7/2007 |
| WO | 2010131210 A1 | 11/2010 |
| WO | 2012135977 A1 | 10/2012 |

* cited by examiner

DEVICE, METHOD AND SYSTEM FOR GENERATING DYNAMIC PROJECTION PATTERNS IN A CONFOCAL CAMERA

FIELD

The present application relates generally to a device for generating dynamic projection patterns in a confocal camera, and, more particularly, to a device, method and system for utilizing an optical array generator, confocal measurement/depth of focus techniques to generate dynamic patterns in a camera for projection onto the surface of an object for three-dimensional (3D) measurement. This may involve, for example, fringe projection methods, structured light projected onto an object's surface produces illumination that appears blurred and may be used for an exact geometric reconstruction of the surface shape.

DESCRIPTION OF RELATED ART

In fringe projection methods, objects may illuminated with structured patterns of light such as sinusoidal fringe patterns. The structured patterns may phase modulated by the objects and then recorded as images with a camera at a known angle with respect to the projections. Techniques such as Fourier transforms may be used to calculate the phase modulations by analyzing the recorded images. Using a suitable phase unwrapping algorithm, a continuous phase distribution which may be proportional to the object height variations may be obtained and the system may be calibrated to map the unwrapped phase distribution to real world 3D coordinates.

Specifically 3D information may obtained by taking an image of the object in an observation angle that may be tilted an angle to the direction of projection of structured light/ projected pattern. The projected pattern may then be distorted according to the surface shape of the object. The features of the projected pattern may be matched to the corresponding features in the distorted image by means of image processing algorithms. A problem arises if the object being measured is translucent. Light penetrates into the translucent object and may be diffused in its depth. Examples of such material may include wax, skin or teeth. As a result, the contrast of the pattern on the object surface may decrease significantly, since the diffuse, unstructured scattered light from the object's depth may be superimposed on the desired light reflected by the surface of the object. A reduced contrast may result in the inability to detect the projected features since the noise may become greater than the signal amplitude. A possible improvement in this situation may be to increase the amount of light on the sensor to reduce the sensor's shot noise relative to the signal. However, this may be technically limited by the full-well capacities of the image sensor pixels. Furthermore, the "object noise" (disturbances caused by the object itself e.g. from a rough surface or a non-uniform coloring) may not be reduced by increasing the amount of light. In addition, some devices that attempt to solve these problems employ constructions that bulky and use large amounts of space.

U.S. Pat. No. 7,852,492 B2 describes a device for the tomographic scanning of objects comprising a first grid arranged in an optical axis of a light beam downstream of a source of light through which the light beam may be guided before irradiating an object so that a pattern of the first grid may be projected on the object; an optical imaging assembly for imaging the object on a sensor; and a second grid provided in the optical axis of the reflected light beam, the second grid having a pattern matching the first grid, the reflected light beam having the pattern of the first grid being guided through said second grid so that the sensor senses the light beam reflected by the object with a Moiré pattern resulting from overlying the pattern of the first grid and the pattern of the second grid. U.S. Pat. No. 7,852,492 B2 is hereby incorporated by reference for all purposes.

U.S. patent application Ser. No. 15/021,588 illustrates an optical system for generating an illumination patterns which changes over time wherein optical arrangements such as via pockel cells, rotating polarizers and structured retarders leads to switchable polarization directions of a light source. It is hereby incorporated by reference for all purposes.

SUMMARY

Existing limitations associated with the foregoing, as well as other limitations, may be overcome by a device, method and system for utilizing an optical array generator, confocal measurement/depth of focus techniques to generate dynamic patterns in a camera for projection onto the surface of an object for three-dimensional (3D) measurement, while reducing noise and increasing data density for three-dimensional (3D) measurement. Herein, projected light patterns may be used to generate optical features on the surface of an object to be measured and optical 3D measuring methods which operate according to triangulation, confocal measurement/depth of focus principles may be used to measure the object. Herein a temporal varying light may be projected onto an object to be imaged by the camera. A variable imaging optics having a depth of focus that may be much smaller than the thickness of the object may be used in projection and detection. The variable imaging optics may be a movable imaging optics, liquid lenses, flexible lenses or the like. Thus the temporal varying light pattern may be imaged sharply (or with maximum contrast), only in the regions of the object that intersect with the depth of focus of the variable imaging optics. By the use of the variable imaging optics, the focal plane of the imaging optics may be moved through the volume of the object. In off-focus regions the light blurs and creates a constant average intensity that distinguishes the off-focus regions from the focused regions. Only the focused regions/sharply imaged regions of the object may therefore create a modulated signal on the image sensor. By using various structured illumination patterns, confocal measurement/depth of focus principles, along with noise reduction and data density increasing setups/techniques, 3D surface profiles of objects may be measured. Moreover, by modulating with a certain frequency, only signals corresponding to that frequency may be detected for further processing.

In one embodiment, an optical array generator for generating projection patterns may be provided in a camera. The optical array generator comprises a collimator, an LED array and a lens array (also referred to as microlens array). The collimator may be constructed to direct light of the LED array onto the lens array which comprises sub lenses. Each sub lens of the lens array may be constructed to produce an image of the LED array. As such an image produced by the LED array may be multiplied into an array of sub-images by the lens array. The sub-images of lens array combine in the focal plane of the lens array to form a combined image. Lenses of the lens array may be biconvex to allow for a high light efficiency due to the use of high numerical apertures in the illumination path. In another embodiment, a camera may be provided with projection optics to project the combined image onto a surface of the object to be measured. In an embodiment herein, the images produced by the LED array for conversion into sub-images may be structured and variable (non-static). In an embodiment, the light source may comprise LED dies. In another embodiment, laser diodes or other light emitting elements may be used. In yet another embodiment, the light source may be formed on one end of a plurality of optical fibers that have light sources attached to the other end. In yet another embodiment, multiple collimators each having multiple light sources may be used. In yet another embodiment the light source comprises at least two discrete regions in a common housing.

According to another example embodiment herein, a camera system is provided. The camera system may include an optical array generator configured to generate projection patterns onto an object to be measured, a sensor for recording reflected projection patterns, and a digital signal processing unit for processing the recorded images. In an embodiment, the sensor may be a sensor with an in pixel demodulation function wherein the sensor comprises a photodiode, preamplifier synchronous demodulator and an integrator. In another embodiment, the sensor may be a 2D-sensor for recording a continuous sequence of images for different projection patterns generated by the optical array generator. In another embodiment, the system comprises an acquisition unit for further processing the recorded images and displaying a three-dimensional measurement of the object. According to an embodiment herein, light from a source having multiple discrete regions, wherein each region may be electronically controlled individually, may be directed by a collimator to a lens array to produce a combined image comprising sub-images in a focal plane of the lens array, which combined image may be projected onto the object being measured by a variable imaging optics which may be used for illumination and detection. Through the use of the variable imaging optics, the focal plane of the variable imaging optics may be moved through the volume of the object being measured. Stripes of the combined image may only be visible if the focal plane of the variable imaging optics coincides with the object surface. In an embodiment herein, a continuously moving pattern may be generated on the object surface by using, for example, at least three light sources and lighting them sequentially. Images including diffused background light may be reflected from the object and the variable imaging optics and a beam splitter direct the reflected images to a sensor to be recorded.

According to another example embodiment herein, a method for utilizing an optical array generator, confocal measurement/depth of focus techniques to generate dynamic patterns in a camera for projection onto the surface of an object for three-dimensional (3D) measurement is provided.

According to an example embodiment herein, the method comprises generating a plurality of projection patterns from an LED array, directing each plurality of the projection patterns of the LED array onto a lens array using a collimator, producing sub images of each plurality of the projection patterns with sub lenses of the lens array wherein the sub images may be formed in a focal plane of the lens array to form a combined image, imaging the combined image onto a surface of the object to be measured, recording a reflected image from the surface of the object with a sensor and processing the recorded image to obtain a three-dimensional image of the object. In an embodiment, the light source comprises at least two discrete regions and the light source may be controlled by switching such that a periodic pattern may be formed which may be imaged onto an object. By switching the discrete regions of the light source, the pattern may be varied in the focal plane of the lens array. Depending on the arrangement of the discrete regions of the light source and the design of the lens array (e.g. spherical lenses or cylindrical lenses), complementary checkerboard patterns or complementary stripe patterns may be generated. Rapid switching of the light sources creates a fast change of the complementary illumination patterns and thus a spatial and temporal modulation. In an embodiment herein, the projection pattern in the image plane of the lens array may be shifted by shifting the light source such that lateral fine adjustment of the projection pattern may be achieved. Herein, in an embodiment wherein a magnification of the array generator may be M=15:1, a required alignment accuracy of, for example, 1 micron of the lens array may be reduced to an alignment accuracy of 15 microns of the LED board.

In another embodiment herein, in addition to the light source for the pattern projection, other light sources may be added in the object plane of the collimator for additional lighting tasks such as for providing colored 2D images. In yet another embodiment, the use of a collimator with aspherical lenses may be employed. In another embodiment, an illuminating lens may be used to project the pattern onto the object, wherein the depth of focus of the lens may be much smaller than the thickness of the object being measured. The smaller the depth of focus, the smaller is the range in the z-direction where the stripe pattern may be seen sharply on the object. Accordingly the lens position that produces the sharpest stripe pattern for a certain region of the object may be determined more accurately.

In another embodiment, the recording step may be performed with a sensor provided with an in pixel demodulation function wherein the sensor may comprise a photodiode, preamplifier, synchronous demodulator and/or an integrator. In another embodiment, the recording step may be performed with a 2D sensor for recording a continuous sequence of images for different projection patterns generated by the optical array generator. In another embodiment, the processing step may comprise locating projected features in the recorded images and processing the recorded images into a three-dimensional measurement of the object.

The device method and system may be useful for reducing the noise generated in three dimensional measurements and to increase the density of data gathered when scanning an object.

Further features and advantages, as well as the structure and operation of various embodiments herein, are described in detail below with reference to the accompanying drawings.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein and wherein.

Figure 1:
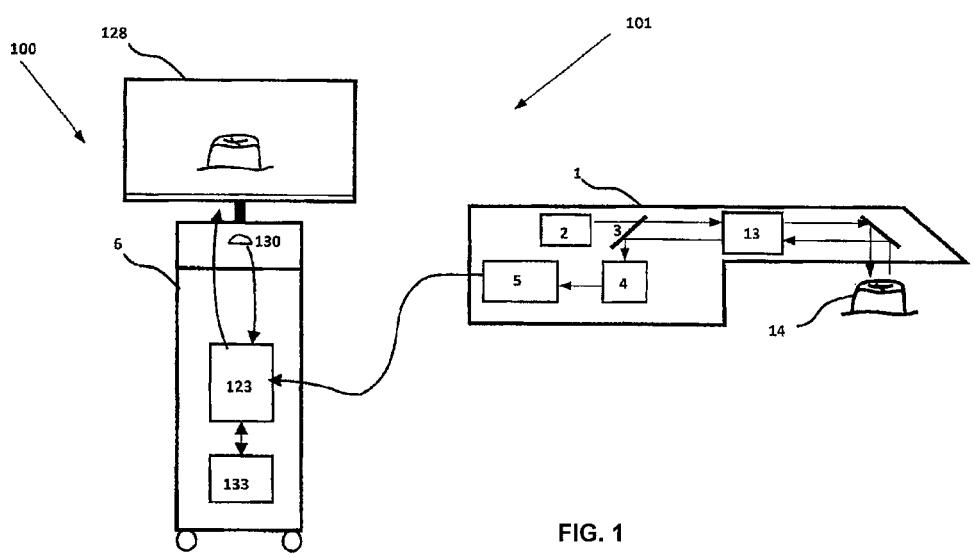
FIG. 1 is a system illustrating how projection patterns may be used in a confocal camera to measure an object

Different ones of the Figures may have at least some reference numerals that may be the same in order to identify the same components, although a detailed description of each such component may not be provided below with respect to each Figure.

DETAILED DESCRIPTION OF THE PREFERRED EMBODIMENTS

In accordance with example aspects described herein, a device, method and system may be provided for utilizing an optical array generator, confocal measurement/depth of focus techniques to generate dynamic patterns in a camera for projection onto the surface of an object for three-dimensional (3D) measurement.

Optical Array Generator, Camera and Camera System

FIG. 1 illustrates a block diagram of a camera system 101 comprising a camera 1, for example a dental camera, for generating dynamic patterns, and which may be constructed and operated in accordance with at least one example embodiment herein. The system also comprises a computer system 100 for generating and displaying three dimensional representations of an object. The computer system 100 may be electrically connected to the camera 1. The camera may include an optical array generator 2 comprising a spatially and temporally modulated light source wherein the light source (e.g. LED array 20) comprises discrete regions that may be controlled electronically individually. The optical array generator 2 also comprises a collimator 21, and a lens array 22 comprising sub lenses 25 for generating a combined image 27 of the LED array. The combined image 27 may comprise sub images 26 wherein each sub lens may generate a sub image 26 (26A', 26B'). An imaging optic 13 projects the combined image onto the object 14 to be measured. In an embodiment herein, the imaging optic 13 projects an illumination beam 62 comprising varying combined images onto the object 14 during a scanning process or exposure. The object may be for example a tooth or otherwise object. The variable imaging optic 13 may also receive and image reflected images from the tooth onto the sensor 4. In another embodiment herein, the imaging optic 13 receives a monitoring beam 63 comprising varying reflected images (not shown) from the object 14 during a scanning process or exposure. The received images may be propagated by beam splitter 3 to a sensor 4 to be recorded. In one exemplary embodiment, a standard 2D sensor may be used for the acquisition. In this case the demodulation may be done in a separate computation unit like a CPU. Herein, the modulation frequency may be limited by the read out frequency of the 2D sensor. If, for example, a high speed 2D sensor may be used with a frame rate of 5000 pictures per second, the maximum demodulation frequency may be 2500 Hz. (e.g. the frame rate may be between 500 frames/s and 10,000).

In another exemplary embodiment, the sensor may be a sensor with in-pixel demodulation function wherein each pixel of the sensor may include of a photodiode, a pixel integrator, a preamplifier, a synchronous demodulator and/or an integrator. The photodiode of each pixel converts the light from the object 14 into photocurrent. The photocurrent may be then integrated during each half of the modulation period (e.g. between 2 µs-50 µs or between 0.01 µs-1 ms), amplified and fed into the synchronous demodulator. The demodulator may be synchronized by the modulation signal of the light source of the optical array generator 2. It may be seen that the modulation frequency may be limited only by the light source. As such, the frequency used for modulation may be up in the MHz range if suitable LEDs or laser diodes may be used. Using a high modulation frequency (such as between 20 kHz-500 kHz or between 1 kHz-100 MHz) may have the advantage, that the pixel integrators may not be saturated, even when very high illumination intensities are be used. A good choice for the modulation frequency may be about 5-100 modulation periods for one demodulated image in order to avoid saturation of the pixel integrators. The demodulator output may be summed over the exposure time by the integrator. At the end of the exposure, the integrated signal may be proportional to the amplitude of the light modulation. Constant background light may be suppressed by the demodulation. For read out, the pixels of the image matrix may be addressed sequentially by a switch matrix and the voltages of the integrators may be digitized and transferred to the digital signal preprocessing unit 5.

A depth of focus technique is used in the confocal camera 1 wherein for a given pattern from the light source 10 incident on the imaging optics 13, the depth of focus may be the range of image distances from the imaging optics 13 for which the pattern 15 is in focus on the object 14 and wherein for a given reflected pattern from the object 14 incident on the imaging optics 13 the depth of focus may be the range of image distances from the imaging optics 13 for which the reflected pattern is in focus on the sensor 4. Herein the position of the image depends on the source of light. More particularly, during projection of an image onto one or more objects (e.g., teeth), the image may be sharp or in focus only on surfaces of the one or more objects that are within the depth of focus. During detection of reflected images, only images that are in focus may be formed on the sensor by, for example, using an appropriately positioned aperture (not shown) to let in focus images onto the sensor 4 and block out of focus images.

During the exposure/scan, the digital signal preprocessing unit 5 may collect the single image frames of the sensor 4 and build an image stack in the local memory of this unit. Subsequently the data volume may be reduced by discarding all data points of the image stack that contain no signal since they may not be part of the object's surface. Finally the remaining data may be transmitted to the acquisition unit 6 which may be part of a computer system 100 comprising the acquisition unit 6 and a display 128. The acquisition unit may further comprise a computer processor including a central processing unit (CPU) 123 and a random access memory (RAM) 133.

In an embodiment, the digital signal processing includes the steps wherein, for each sensor pixel, the maximum amplitude may be determined across the image stack. Because each image corresponds to a known position of the variable imaging optics, the z-position of the object surface, seen according to the pixel, may be calculated by use of calibration data.

In an embodiment herein, an image stack from the preprocessing unit 5 may be received by the CPU 123 and may be temporarily stored in the RAM 133. It may then be analyzed by looking for the maximum amplitude of each xy-pixel along the z-axis of the stack. Each found maximum corresponds to a point (x,y,z) on the surface of the object. A distortion correction applied to the points corrects for the imaging properties of the optics. When the camera is moved while recording, a series of point clouds results, which shows different sections of the object 14 from different viewpoints. These point clouds may be rotated and translated individually by the CPU 123 to give a consistent 3D-model. This 3D-model may finally be rendered on the display 128.

Figure 3:
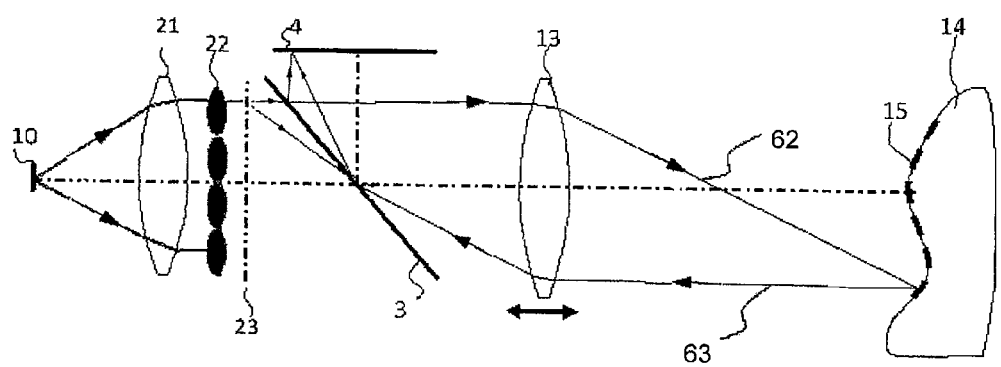
FIG. 3 is a schematic representation of a projector for structured illumination.
Figure 5:
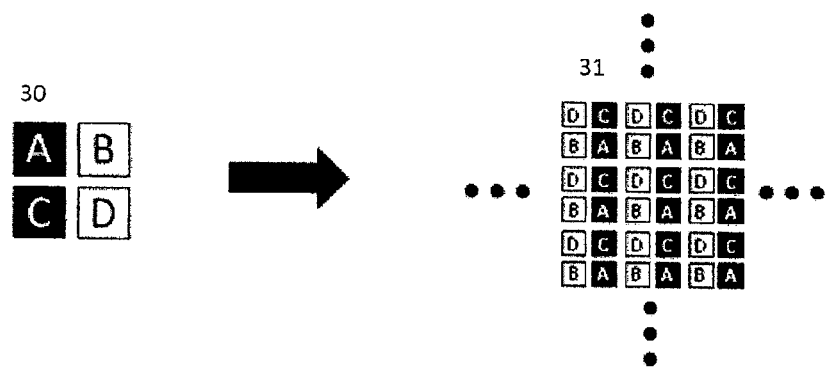
FIG. 5 illustrates the generation of dot patterns with arrays of spherical lenses according to an embodiment herein.
Figure 6:
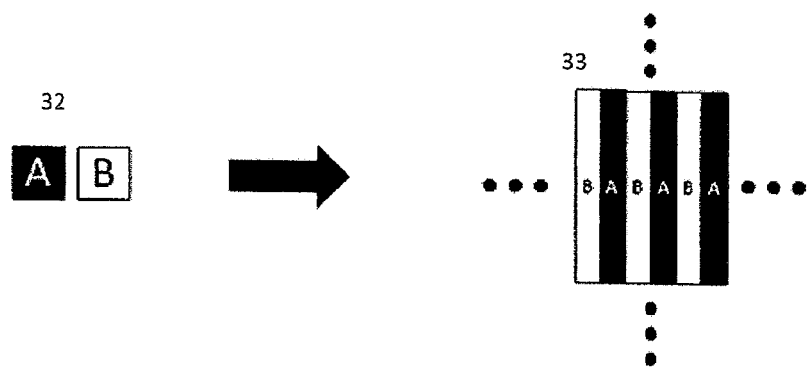
FIG. 6 illustrates the generation of stripe patterns with a cylindrical lens array according to an embodiment herein.

In FIG. 3, light source 10 (such as for example an LED array 20 with a collimator 21) illuminates a lens array 22 to form a combined image in a focal plane 23 of the lens array 22. The light source may comprise at least two adjacent discrete regions that may be individually controlled electronically. This arrangement of the light source may be further imaged into sub-images having a periodic pattern by the lens array 22. In the focal plane of the lens array, the periodic pattern may be formed which may be imaged onto the object 14 by a variable imaging optics 13. By switching the discrete regions of the light source, the pattern may be varied in the focal plane 23 of the lens array 22. Depending on the arrangement of the discrete regions of the light source and the design of the lens array 22 (e.g. spherical lenses or cylindrical lenses), complementary checkerboard patterns or complementary stripe patterns may be generated as shown in FIG. 5 and FIG. 6. Rapid switching of the discrete regions of the light source creates a fast change of the complementary illumination patterns and thus generates a spatial and temporal modulation for projection to the object 14 as projected images 15 by the variable imaging optics 13. The variable imaging optics 13 may be used in reverse to image the object via the beam splitter 3 onto an image sensor 4. For projection, the variable imaging optics 13 may have a depth of focus that may be much smaller than the thickness of the object. Thus the temporal varying light pattern generated by 10, 21, and 22 may be imaged sharply, only in the regions of the object that intersect with the depth of focus of the variable imaging optics 13. By the use of the variable imaging optics (13), the focal plane of the imaging optics may be moved through the measuring volume. In off-focus regions the pattern blurs and creates a constant average intensity. In turn, only the sharply imaged regions of the object may create a modulated signal on the image sensor 4. In an embodiment, the sensor 4 may have specially designed pixels that may be sensitive to modulated light and may suppress a constant background signal. The output image of the sensor may therefore be a height (contour) line, tracing the intersection of the object surface and the variable imaging optics 13 depth of focus. Using the variable imaging optics 13 an image stack with intersection at different heights may be recorded. By appropriate evaluation of the image stack, such as the maximum amplitude analysis of each xy-pixel along the z-axis, the object may be reconstructed three-dimensionally.

Figure 4:
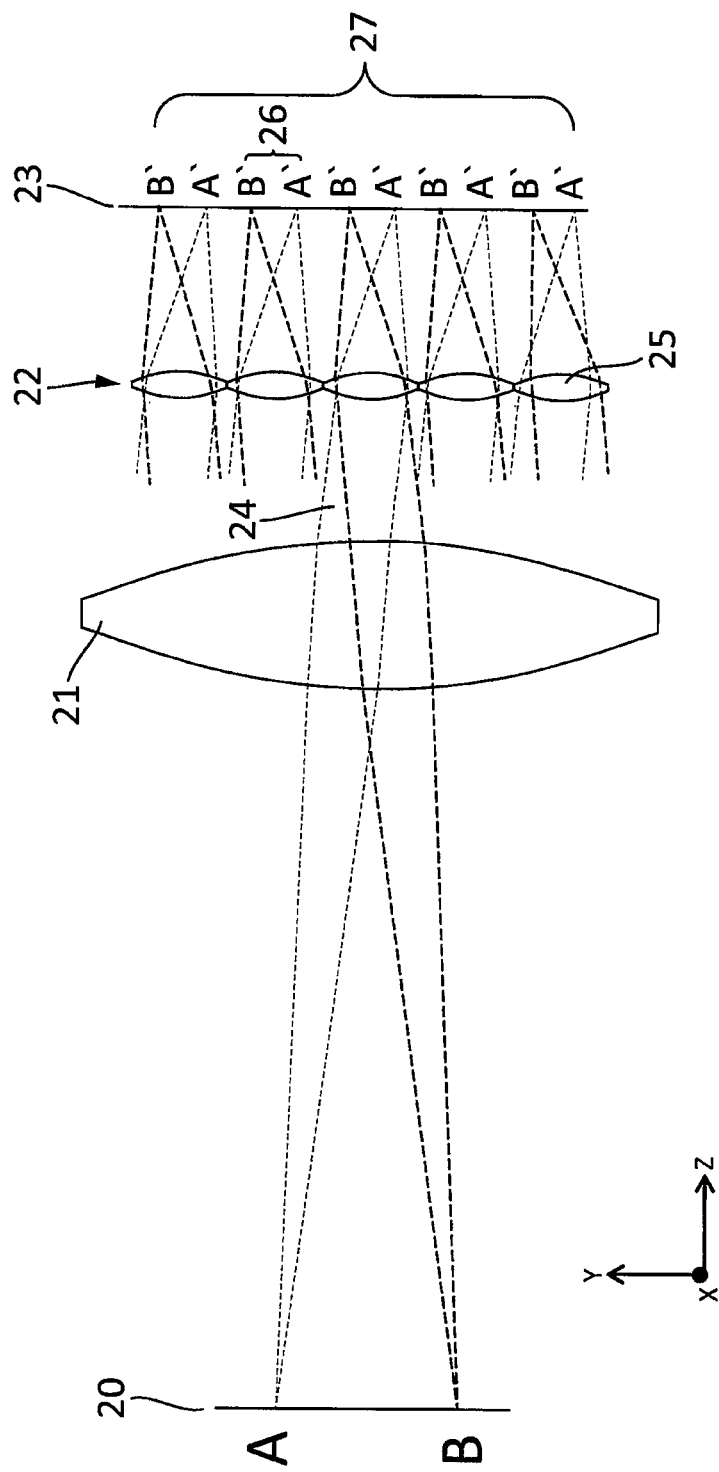
FIG. 4 illustrates an optical array generator according to an embodiment herein.

In FIG. 4 a schematic representation of the optical array generator 2 for generating time varying dynamic patterns is shown. FIG. 5 illustrates a top view of an example LED array 20 of the optical array generator 2 according to an embodiment herein. As shown in FIG. 4, collimator 21 directs the light of an LED array 20 onto a lens array 22. Each sub-lens 25 of the lens array may produce a sub-image 26 of the LED array. The sub-images 26 combine in the focal plane 23 of the lens array 22 to form a combined image 27. The combined image 27 in this plane may then be imaged onto the object surface by means of the imaging optics 13 (projection optics) of the camera 1. In an example embodiment herein, as shown in FIG. 4, two light sources (A, B) of the LED array 20 may be placed in the object plane (X-Y plane) of the collimator 21. Behind the collimator 21, the beams originating from the light sources, form two parallel bundles of rays 24. The beams may be focused by the lens array 22 into an image plane 23. Each individual lens generates one focus pair (A', B'). The offset between the focus points A' and B' may be determined by the choice of the incidence angle of the parallel beams and the focal length of the lens array. In an embodiment, multiple collimators 21 and multiple light sources may be used, though not required. Herein, a light source may be coupled with a collimator 21. Individual collimators may be aligned directly under the required angle of incidence to the lens array 22. The angle of incidence may depend on the optical design of the camera and may be, for example, between 2°-10° or between 0.1°-30°) However, in another embodiment, space may be saved with the design of the camera, by aligning the collimators in parallel and setting the angle of incidence of light to the lens array 22 using deflecting elements e.g. mirrors. In another embodiment herein, the LED array 20 may be a 2×2 LED array 30 as shown in FIG. 5 or otherwise LED array.

Figure 7:
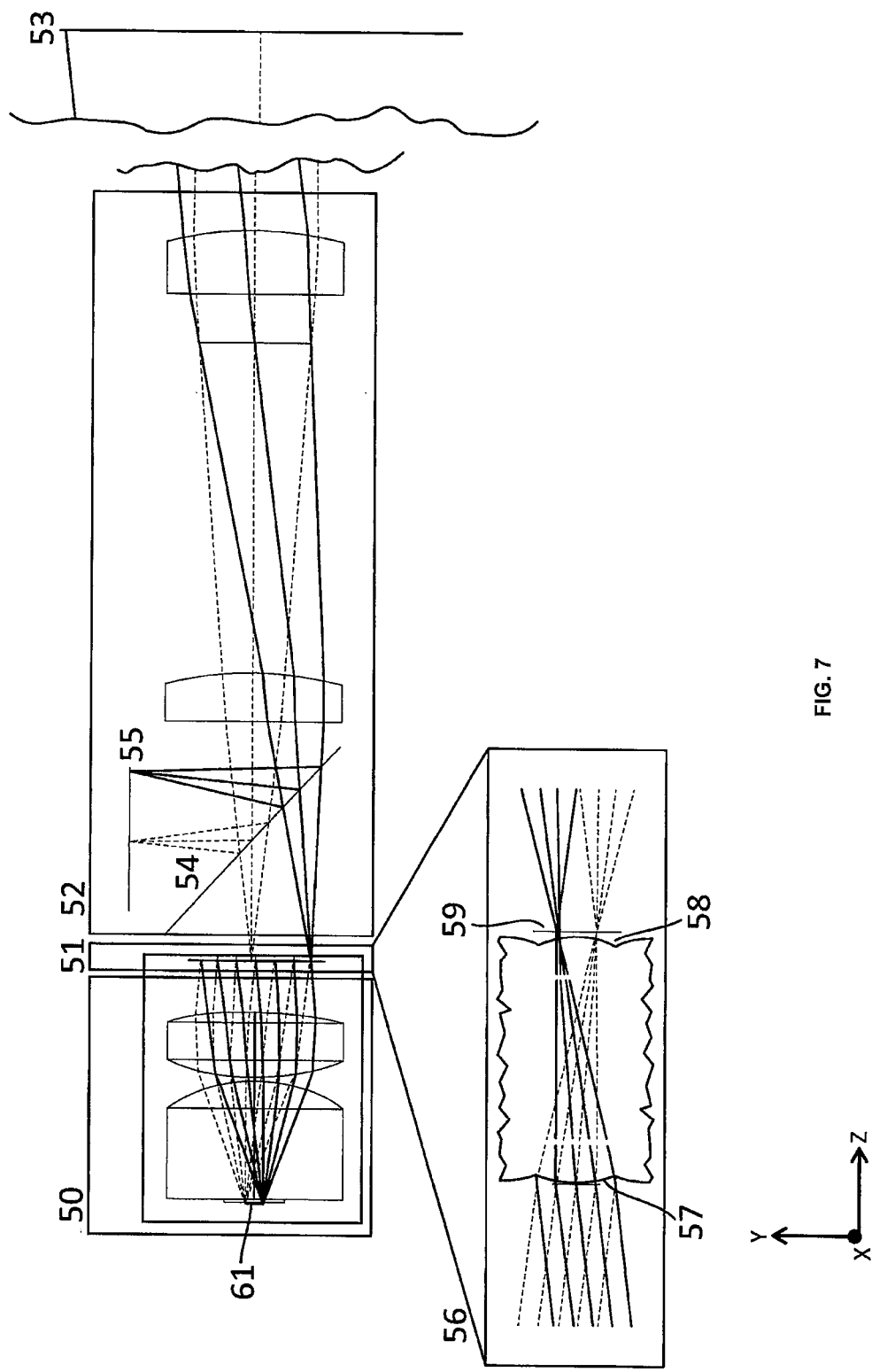
FIG. 7 illustrates an exemplary embodiment discussed herein.

FIG. 7 illustrates another embodiment herein. A collimator assembly 50 may focus the light from, for example, two LED chips 61 onto a lens array 51. In an embodiment herein, the centers of the two LED dies may be spaced, for example 1.5 mm apart (or for example between 0.5 mm-15 mm apart) and the collimator may have an effective focal length of for example 10 mm (or for example, between 3 mm-100 mm). This results in a tilt angle of a tan ((1.5 mm/2)/10 mm)=4.3° (or for example between 2°-10° or between 0.1°-30°) for the parallel light bundles exiting the collimator assembly 50. Due to a refractive index of, for example, n=1.52 of the lens array 51, the angle may be reduced to 2.8° relative to the optical axis (z-axis) in the substrate of the array. From a requirement that the stripes should have a spacing (center of stripe A to center of adjacent stripe B in FIG. 6) of 100μ (or for example between 2μ to 200 μm), it thus results in a thickness of the lens array of (100 μm/2)/tan (2.8°)=1.0 mm (or for example between 50 nm to 10 mm). The pitch of the lens array (center of a lens to center of adjacent lens) may be twice the stripe spacing (200 nm). Section 56 shows an enlarged, single pair of lenses of the array in cross section. The lens array may be designed as a thin plate, which carries lenses on both sides. The entrance lenses 57 act as Fourier lenses and generate images of the light sources in the focal plane 59. The exit lenses 58 act as field lenses. The combined image of the light sources in the plane 59 may be projected onto the object 53 by the imaging optics 52. By means of the same imaging optics and the beam splitter 54, an image of the object may be finally produced on the sensor 55.

Computer System for Generating Dynamic Patterns in a Camera for 3D Measurement

Having described a system 101 for generating dynamic patterns in a confocal camera for projection onto the surface of an object for three-dimensional (3D) measurement, reference will now be made to FIG. 2, which shows a block diagram of a computer system 100 that may be employed in accordance with at least some of the example embodiments herein. Although various embodiments may be described herein in terms of this exemplary computer system 100, after reading this description, it may become apparent to a person skilled in the relevant art(s) how to implement the disclosure using other computer systems and/or architectures.

In one example embodiment herein, at least some components of the computer system 100 may form or be included in the computer system 100 of FIG. 1. The computer system 100 includes at least one computer processor 122. The computer processor 122 may include, for example, a central processing unit 123 as shown in FIG. 1, a multiple processing unit, an application-specific integrated circuit ("ASIC"), a field programmable gate array ("FPGA"), or the like. The processor 122 may be connected to a communication infrastructure 124 (e.g., a communications bus, a cross-over bar device, or a network). In an embodiment herein, the processor 122 includes a CPU 123 that obtains an image stack from the preprocessing unit 5 of the camera 1 having a sensor 4 with an in-pixel demodulating function. The stack may be temporarily stored in memory and then analyzed. Upon moving the camera 1 while recording, a series of point clouds may be formed. The CPU 123 may rotate and translate the point clouds to give a consistent 3D-model for rendering on the display interface 126 of the computer system 100. In another embodiment, the CPU may match image features detected by the sensor 4 to the projected features and convert them to a 3D-point cloud by triangulation with each image resulting in a separate point cloud. Herein, the sensor may optionally not possess in-pixel demodulating functionality. When the camera is moved a series of point clouds results. These point clouds may be rotated and translated individually by the CPU 123 to give a consistent 3D-model. This 3D-model may be finally rendered on the display 128. In yet another embodiment herein, the digital signal preprocessing unit 5 of the camera 1 may be incorporated into the computer system 100.

The display interface (or other output interface) 126 forwards video graphics, text, and other data from the communication infrastructure 124 (or from a frame buffer (not shown)) for display on a display unit 128 (which, in one example embodiment, may form or be included in the display unit 128 of FIG. 1). For example, the display interface 126 may include a video card with a graphics processing unit.

The computer system 100 may also include an input unit 130 that may be used by a user of the computer system 100 to send information to the computer processor 122. In one example embodiment herein, the input unit 130 may form or be included in the input unit 130 of FIG. 1. The input unit 130 may include a trackball or other input device such as a keyboard and/or touchscreen monitor. In one example, the display unit 128, the input unit 130, and the computer processor 122 may collectively form a user interface.

One or more steps of generating the dynamic patterns may be stored on a non-transitory storage device in the form of computer-readable program instructions. To execute a procedure, the processor 122 loads the appropriate instructions, as stored on storage device, into memory and then executes the loaded instructions.

Figure 2:
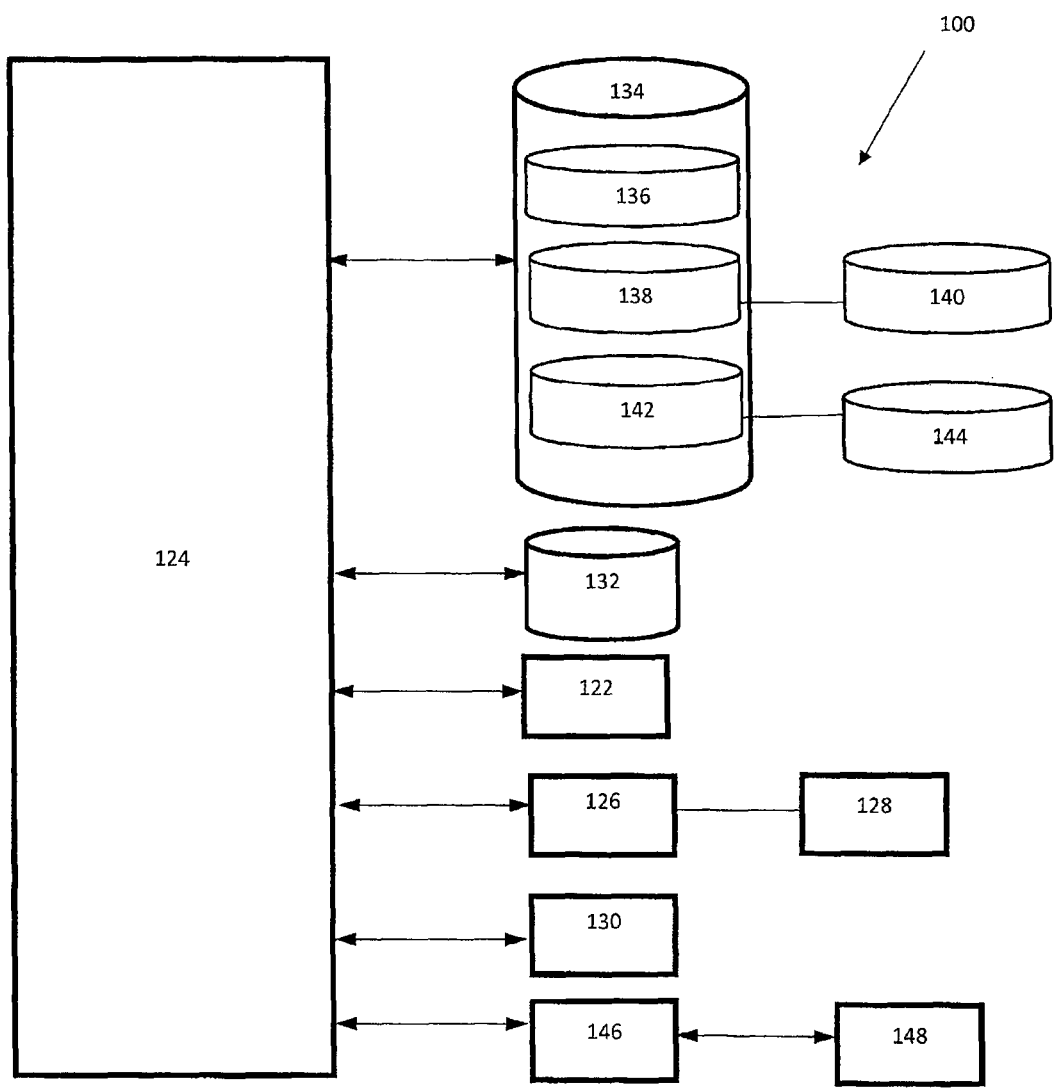
FIG. 2 illustrates a block diagram of an example computer system of the system of FIG. 1.

The computer system 100 of FIG. 2 may comprise a main memory 132, which may be a random access memory ("RAM") 123 as shown in FIG. 1, and also may include a secondary memory 134. The secondary memory 134 may include, for example, a hard disk drive 136 and/or a removable-storage drive 138 (e.g., a floppy disk drive, a magnetic tape drive, an optical disk drive, a flash memory drive, and the like). The removable-storage drive 138 reads from and/or writes to a removable storage unit 140 in a well-known manner. The removable storage unit 140 may be, for example, a floppy disk, a magnetic tape, an optical disk, a flash memory device, and the like, which may be written to and read from by the removable-storage drive 138. The removable storage unit 140 may include a non-transitory computer-readable storage medium storing computer-executable software instructions and/or data.

In further alternative embodiments, the secondary memory 134 may include other computer-readable media storing computer-executable programs or other instructions to be loaded into the computer system 100. Such devices may include a removable storage unit 144 and an interface 142 (e.g., a program cartridge and a cartridge interface); a removable memory chip (e.g., an erasable programmable read-only memory ("EPROM") or a programmable read-only memory ("PROM")) and an associated memory socket; and other removable storage units 144 and interfaces 142 that allow software and data to be transferred from the removable storage unit 144 to other parts of the computer system 100.

The computer system 100 also may include a communications interface 146 that enables software and data to be transferred between the computer system 100 and external devices. Such an interface may include a modem, a network interface (e.g., an Ethernet card or an IEEE 802.11 wireless LAN interface), a communications port (e.g., a Universal Serial Bus ("USB") port or a FireWire® port), a Personal Computer Memory Card International Association ("PCM-CIA") interface, Bluetooth®, and the like. Software and data transferred via the communications interface 146 may be in the form of signals, which may be electronic, electromagnetic, optical or another type of signal that may be capable of being transmitted and/or received by the communications interface 146. Signals may be provided to the communications interface 146 via a communications path 148 (e.g., a channel). The communications path 148 carries signals and may be implemented using wire or cable, fiber optics, a telephone line, a cellular link, a radio-frequency ("RF") link, or the like. The communications interface 146 may be used to transfer software or data or other information between the computer system 100 and a remote server or cloud-based storage (not shown).

One or more computer programs or computer control logic may be stored in the main memory 132 and/or the secondary memory 134. The computer programs may also be received via the communications interface 146. The computer programs include computer-executable instructions which, when executed by the computer processor 122, cause the computer system 100 to perform the methods as described hereinafter. Accordingly, the computer programs may control the computer system 100 and other components of the camera system 101.

In another embodiment, the software may be stored in a non-transitory computer-readable storage medium and loaded into the main memory 132 and/or the secondary memory 134 of the computer system 100 using the removable-storage drive 138, the hard disk drive 136, and/or the communications interface 146. Control logic (software), when executed by the processor 122, causes the computer system 100, and more generally the camera system in some embodiments, to perform the some of the methods described hereinafter.

Lastly, in another example embodiment hardware components such as ASICs, FPGAs, and the like, may be used to carry out the functionality described herein. Implementation of such a hardware arrangement so as to perform the functions described herein will be apparent to persons skilled in the relevant art(s) in view of this description.

Method for Generating Dynamic Patterns in a Camera for 3D Measurement.

Having described the computer system 100 of FIG. 2, the camera system 101 will now be further described in conjunction with FIG. 4-6 which show methods of generating projection patterns using different lens types.

Turning now to FIG. 5 and FIG. 6, complementary checkerboard patterns, complementary stripe patterns, or otherwise complementary pattern may be generated. As shown in FIG. 5, which shows the generation of patterns using a lens array 22 comprising spherical lenses, if LEDs A and C of the LED arrangement 30 are switched on (left side), a stripe pattern may be produced in the image plane of the lens array 22 (right side). When LEDs B and D are turned on, and LEDs A and C are turned off, a complementary stripe pattern may be created. In an embodiment herein, the intensity of each LED/die in the LED array 20 may be controlled individually.

As shown in FIG. 6, which shows the generation of fringe patterns using a lens array 22 comprising cylindrical lenses, each lens generates a pattern with all patterns combining to form the stripe patterns produced in the image plane of the lens array 22. Mutual switching of the LEDs thus again results in complementary fringe patterns.

In another example embodiment herein, the microlens array 22 is preferably aligned with the pixels on the sensor or detector pinholes (not shown). By displacing the light sources laterally in the object plane of the collimator 21, the multiplied pattern in the image plane 23 of the microlens array 22 may also be shifted. This may be used to perform a lateral fine adjustment of the pattern.

Using a magnification of the optical array generator, the alignment/positioning accuracy of the microlens array may be controlled by the alignment/positioning accuracy of the LED array such that instead of directly changing the alignment of the microlens array, the LED array may be rather displaced to produce correct alignment of the microlens array, without moving the microlens array itself. For example, in an embodiment herein where the magnification of the array generator may be M=15:1, a required alignment accuracy of 1 micron of the lens array may thus be reduced to an alignment accuracy of 15 microns for the LED board. Herein, the alignment accuracy of 15 microns for the LED board may be easier to achieve.

In another embodiment herein, in addition to the light sources used for the pattern projection, further light sources may be added in the object plane of the collimator 21 for additional lighting tasks. For example, if a confocal scanner that uses monochromatic light for 3D-measurement is also required to provide colored 2D-images, the object may be at least shortly illuminated with light sources of different colors. This may be archived by placing LED-dies of different colors next to the LED-dies used for the stripe projection. Herein, additional collimators and coupling optic such as dichroic beam splitter may be avoided.

An additional unwanted AC-offset may arise, even in object regions that are off-focus if the irradiance of the lens array 51 of FIG. 7 does not remain locally constant when the light sources are switched over. To avoid this, the collimator assembly 50 may be optically corrected (for example by adding additional lenses or using aspherical lenses) so that a homogeneous illumination (and angle of incidence) of the lens array 51 may be ensured, although the light sources in the collimator may be offset with respect to the optical axis. Alternatively, highly efficient collimator optics, with high numerical aperture (NA) may be required. These requirements may be realized efficiently by the use of aspherical lenses. Therefore in an embodiment herein a collimator with aspherical elements may be used.

In another example embodiment herein, in order to guide light behind the lens array 51, for projection onto the object 53, biconvex lenses may be used for the lens array 51. The lenses on the exit side of the array may thus act as field lenses to ensure that beam cones behind the foci are perpendicular to the image plane (see exemplary embodiment, FIG. 7, wherein the exit lenses 58 act as field lenses).

Advantages of the embodiments described herein may include compactness and robustness, as there are no grid structures and no moving parts in the pattern generation. Further, since there are no elaborate or complicated polarization optics, the cost of the camera may be reduced. Moreover since the optical setup does not include slides or grid structures, all light from the collimator 21 passes through the lens array 22 to the imaging optics 13 without being absorbed and waste heat produced in the camera may be reduced. Moreover, the modulation frequency may be limited only by the light source. In an embodiment, the modulation frequency may be increased to the MHz range (for example between 1 kHz-100 MHz) by using suitable LEDs or laser diodes.

In view of the foregoing description, it may be appreciated that the example embodiments described herein provide a device, method and system for generating dynamic projection patterns in a camera.

Unless otherwise defined, all technical and scientific terms used herein have the same meaning as commonly understood by one of ordinary skill in the art to which this invention belongs. Although methods and materials similar to or equivalent to those described herein may be used in the practice or testing of the disclosure, suitable methods and materials are described above. All publications, patent applications, patents, and other references mentioned herein are incorporated by reference in their entirety to the extent allowed by applicable law and regulations. The disclosure may be embodied in other specific forms without departing from the spirit or essential attributes thereof, and it may therefore be desired that the present embodiment be considered in all respects as illustrative and not restrictive. Any headings utilized within the description are for convenience only and have no legal or limiting effect.

What is claimed is:

1. A camera, comprising:
   an optical array generator for generating a plurality of dynamic patterns for projection, the optical array generator further comprising:
   a light source including a plurality of discrete regions wherein a luminous intensity of each of the plurality of discrete regions is controlled independently,
   a lens array comprising a plurality of lenses, and
   a collimator having a single optical axis, said collimator with the single optical axis constructed to direct light of the light source to the plurality of lenses such that each lens of the plurality of lenses that is illuminated by light from the light source, images said light of the light source onto an image plane of the lens array in order to produce the plurality of dynamic patterns;
   an imaging sensor arranged within the camera to record a plurality of reflected images from a surface of an object to be measured;
   a variable imaging optics arranged within the camera to focus the plurality of dynamic patterns onto the surface of the object and to image the plurality of reflected images onto the imaging sensor;
   wherein the variable imaging optics is constructed such that a depth of focus of the variable imaging optics is varied during projection or imaging so that features of the plurality of dynamic patterns are projected onto the object with maximum contrast at the depth of focus or features of the plurality of reflected images are imaged onto the sensor with maximum contrast at the depth of focus.

2. The camera of claim 1, wherein the light source is selected from the group consisting of LED dies, laser diodes and an end of a plurality of optical fibers that have other light sources attached to the other end.

3. The camera of claim 1, wherein the light source includes at least three discrete regions.

4. The camera of claim 1, wherein the depth of focus of the variable imaging optics is substantially smaller than a thickness of the object.

5. The camera of claim 1, wherein the imaging sensor is constructed to perform in-pixel demodulation.

6. The camera of claim 1, wherein the dynamic patterns are complementary checkerboard patterns or complementary stripe patterns.

7. The camera of claim 1, wherein each of the plurality of lenses is cylindrical.

8. A method for generating a plurality of dynamic patterns for measuring an object, the method comprising:
   providing a collimator with a single optical axis;
   electronically controlling the luminous intensities of each of a plurality of discrete regions of a light source to generate structured light for said collimator;
   directing the structured light from the light source to a plurality of lenses of a lens array using the collimator;
   producing sub-images of the structured light using each lens of the plurality of lenses that is illuminated by light from the light source such that the sub-images are formed in an image plane of the lens array to form the plurality of dynamic patterns;
   varying a depth of focus of the variable imaging optics during projection or imaging so that features of the plurality of dynamic patterns are projected onto the object with maximum contrast at the depth of focus or features of a plurality of reflected images are imaged onto an imaging sensor with maximum contrast at the depth of focus.

9. The method of claim 8, further comprising the step of recording the plurality of reflected images from the surface of the object with the imaging sensor to create an image stack.

10. The method of claim 9, further comprising processing the plurality of reflected images to obtain a three-dimensional image of the object by determining for each sensor pixel, a maximum amplitude across the image stack.

11. The method of claim 9, further comprising processing the plurality of reflected images to obtain a three-dimensional image of the object by determining a variable imaging optics position that produces the maximum contrast of the dynamic pattern for a region of the object.

12. The method of claim 8, further comprising aligning the lens array with pixels of the imaging sensor by displacing the light source such that the dynamic patterns in the image plane of the lens array are also shifted.

13. The method of claim 8, further comprising performing lateral fine adjustment by using a magnification of the optical array generator wherein a required alignment accuracy of the lens array is reduced to an alignment accuracy of the light source.

14. A system for generating a plurality of dynamic patterns for measuring an object, the system comprising:
   at least one processor operable to:
      electronically control the luminous intensities of each of a plurality of discrete regions of a light source to generate structured light for a collimator that is constructed to have a single optical axis;
      direct the structured light from the light source to a plurality of lenses a lens array using the collimator having the single optical axis;
      produce sub-images of the structured light using each lens of the plurality of lenses that is illuminated by light from the light source such that the sub-images are formed in an image plane of the lens array to form the plurality of dynamic patterns;
      vary a depth of focus of the variable imaging optics during projection or imaging so that features of the plurality of dynamic patterns are projected onto the object with maximum contrast at the depth of focus or features of a plurality of reflected images are imaged onto an imaging sensor with maximum contrast at the depth of focus.

\* \* \* \* \*